United States Patent
Wilmes

(10) Patent No.: US 9,678,095 B2
(45) Date of Patent: Jun. 13, 2017

(54) PIPETTING DEVICE

(71) Applicant: Siemens Healthcare Diagnostics Products GmbH, Marburg (DE)

(72) Inventor: Hugo Wilmes, Bad Soden (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 0 days.

(21) Appl. No.: 15/154,665

(22) Filed: May 13, 2016

(65) Prior Publication Data

US 2016/0341755 A1 Nov. 24, 2016

(30) Foreign Application Priority Data

May 20, 2015 (EP) .................................... 15168487

(51) Int. Cl.
| | | |
|---|---|---|
| *G01N 35/10* | (2006.01) | |
| *B01L 3/02* | (2006.01) | |
| *G01N 35/00* | (2006.01) | |
| *B01F 11/00* | (2006.01) | |

(52) U.S. Cl.
CPC .......... *G01N 35/1011* (2013.01); *B01L 3/021* (2013.01); *B01L 3/0275* (2013.01); *G01N 35/10* (2013.01); *G01N 35/109* (2013.01); *B01F 2215/0037* (2013.01); *B01L 2200/06* (2013.01); *B01L 2300/06* (2013.01); *B01L 2300/0609* (2013.01); *B01L 2300/18* (2013.01);
(Continued)

(58) Field of Classification Search
CPC ............. G01N 35/10; G01N 2035/103; G01N 2035/1025; G01N 35/1011; G01N 35/109; Y10T 436/2575; B01F 11/0088; B01F 2215/0037; B01L 3/021; B01L 3/0275

See application file for complete search history.

(56) References Cited

U.S. PATENT DOCUMENTS 3,780,992 A * 12/1973 Nishi ...................... B01F 11/04
222/198
5,365,798 A * 11/1994 Kressirer ............ B01F 11/0088
366/140
(Continued)

FOREIGN PATENT DOCUMENTS

| CN | 103941031 | 7/2014 |
|---|---|---|
| DE | 3614961 | 8/1987 |

(Continued)

OTHER PUBLICATIONS

European Search Report of European Application No. 15168487.5-1553 dated Nov. 10, 2015.

*Primary Examiner* — Jennifer Wecker
(74) *Attorney, Agent, or Firm* — Dugan & Dugan, PC

(57) ABSTRACT

The invention relates to a pipetting device (1) for an automatic analysis appliance, wherein the pipetting device (1) comprises a pipetting needle (2) with a longitudinal axis (3), and a device (4) for moving the pipetting needle (2). The pipetting device (1) further comprises a holder (5) for the pipetting needle (2), which holder (5) is mounted on the movable device (4) and to which holder the pipetting needle (2) is releasably connected, and a vibration generator which can set at least the tip of the pipetting needle (2) in vibration, wherein the vibration generator is mounted on the movable device (4).

20 Claims, 8 Drawing Sheets

(52) U.S. Cl.
CPC ............... *B01L 2400/0433* (2013.01); *G01N 2035/00534* (2013.01); *G01N 2035/1058* (2013.01)

(56) References Cited

U.S. PATENT DOCUMENTS

| | | | |
|---|---|---|---|
| 6,447,728 B1* | 9/2002 | Wilmes | G01N 35/10 422/564 |
| 6,532,837 B1* | 3/2003 | Magussen, Jr. | B01L 3/0279 73/864.01 |
| 2006/0093525 A1* | 5/2006 | Brunner | G01F 23/2965 422/509 |
| 2011/0181272 A1* | 7/2011 | Andres | B01L 3/0217 324/207.2 |
| 2014/0065017 A1* | 3/2014 | Herz | G01N 35/109 422/63 |
| 2014/0271405 A1* | 9/2014 | Wilmes | G01N 35/1079 422/511 |

FOREIGN PATENT DOCUMENTS

| | | |
|---|---|---|
| EP | 0569851 | 11/1993 |
| EP | 0994356 | 4/2000 |

\* cited by examiner

PIPETTING DEVICE

CROSS REFERENCE TO RELATED APPLICATION

This claims priority to European Patent Application No. EP 15168487.5, filed May 20, 2015, which is hereby incorporated by reference herein in its entirety for all purposes.

FIELD

The invention relates to a pipetting device for an automatic analyzer and concerns the technical field of automatic in vitro diagnostic systems.

BACKGROUND

Nowadays, many detection and analysis methods for determining physiological parameters in samples of body fluids or in other biological samples are carried out in an automated manner and in large numbers in automatic analysis appliances or so-called in vitro diagnostics systems.

Today's analysis appliances are able to carry out a large number of detection reactions and analyses with one sample. To be able to carry out a large number of tests in an automated manner, various devices are needed for the spatial transfer of measurement cells, reaction containers and reagent containers, e.g., transfer arms with a gripping function, transport belts or rotatable transport wheels, and devices for transfer of liquids, e.g., pipetting devices. The appliances comprise a control unit which, by means of suitable software, is able, largely independently, to plan and work out the work steps for the desired analyses.

Many of the analysis methods used in such automated analysis appliances are based on optical techniques. These methods permit the qualitative and quantitative detection of analytes, i.e., the substances to be detected or to be determined, in samples. Clinically relevant parameters, such as the concentration or activity of an analyte, are often determined by means of a portion of a sample being mixed with one or more test reagents in a reaction vessel, which can also be the measurement cell, as a result of which, for example, a biochemical reaction or a specific binding reaction is started which brings about a measurable change in an optical or other physical property of the test mixture.

It is known that, in automatic analyzers used to test biological body fluids, the required reagents are introduced into a measurement cuvette by means of a pipetting device with a pipetting needle. The pipetting device additionally has the role of ensuring that the body fluid to be tested is thoroughly mixed with the reagents. For this purpose, it is necessary to set the pipetting needle in vibration. Hitherto, it was possible to set the pipetting needle in vibration only at defined, stationary positions in an automatic analyzer where vibration generators which cannot be moved are provided (see, for example, EP 0994356 A2). This has the effect that the sample cannot be thoroughly mixed at all positions to which the pipetting needle can be driven. Moreover, thorough mixing of the sample is in principle not possible during a transfer of the pipetting needle from a first position in the analysis appliance to a second position in the analysis appliance. This has the effect of taking up more time and considerably reduces the flexibility in the execution of an analysis in an automatic analysis appliance.

SUMMARY

The object of the invention is therefore to make available a pipetting device which reduces the time taken and permits a greater degree of flexibility in the performance of an analysis in an automatic analysis appliance.

It has been found that an improved pipetting device can be achieved if the vibration generator is mounted on the movable device for moving the pipetting needle.

This has the advantage that the pipetting needle can be set in vibration at every position, and therefore a sample can be thoroughly mixed independently of fixed positions of the pipetting needle. Moreover, mixing is also possible during a transfer of the pipetting needle from a first position in the analysis appliance to a second position in the analysis appliance. This permits, for example, a reduction in terms of time and an increased flexibility in the execution of an analysis in an automatic analysis appliance.

The subject of the present invention is a pipetting device for an automatic analysis appliance wherein the pipetting device comprises a pipetting needle with a longitudinal axis for the pipetting of liquids, a device which is movable in the direction of the longitudinal axis of the pipetting needle and in at least one direction perpendicular to the direction of the longitudinal axis of the pipetting needle and which is used for moving the pipetting needle. Moreover, the pipetting device comprises a holder for the pipetting needle, which holder is mounted on the movable device and to which holder the pipetting needle is releasably connected, and a vibration generator which can set at least the tip of the pipetting needle in vibration. The vibration generator is mounted on the movable device or on the holder for the pipetting needle.

The movable device is preferably designed as an automatically movable robot arm which, for example, is part of an automatic robot station.

In a particularly preferred embodiment, the pipetting device comprises a movable first connection element with a first resetting element, wherein the first connection element produces a releasable connection between the pipetting needle and the vibration generator. The first connection element is preferably movable relative to the pipetting needle in the direction of the longitudinal axis of the pipetting needle. This has the advantage that the releasable connection between the pipetting needle and the vibration generator can be produced and separated in a particularly simple and cost-effective manner. In the operating state of the pipetting device, the pipetting needle is inserted into the holder and the vibration generator is connected to the pipetting needle via the first connection element, such that the vibration generator is able to set the tip of the pipetting needle in vibration. The first resetting element exerts a restoring force on the first connection element, which force keeps the first connection element in a position in which the first connection element produces a connection between the pipetting needle and the vibration generator when the pipetting needle is inserted in the holder.

Preferably, the first connection element has the shape of an angle piece. The angle piece preferably has two limbs which are arranged at right angles to each other. The angle piece is preferably made of metal or plastic. This has the advantage that the releasable connection between the pipetting needle and the vibration generator can be produced and separated in a particularly simple and cost-effective manner. Advantageously, the first connection element in this case has a recess in which an eccentric, which is part of the vibration generator, can engage.

In an advantageous embodiment, the pipetting device comprises a first and a second securing element, wherein the pipetting needle comprises a suspension, and wherein the first securing element is mounted laterally on the suspension and is designed as a blade, and wherein the second securing element is mounted on the holder and is designed as a prism bearing. This has the advantage that the needle according to the invention can be replaced in a way that is particularly easy and uncomplicated. Moreover, this has the advantage that the pipetting needle can be inserted, in particular repeatedly, in a precisely defined position.

In a preferred embodiment, a clamping screw is provided which is able to fix the first connection element in a position. In the operating state of the pipetting device, the clamping screw preferably fixes the first connection element in a position in which the first connection element produces a connection between the pipetting needle and the vibration generator when the pipetting needle is inserted into the holder. The clamping screw is preferably secured on the suspension of the pipetting needle.

When the reagents are being introduced, and during the subsequent actions, there is the danger of the sensitive pipetting needle colliding with the measurement cuvette or other appliance parts, being damaged as a result, and having to be replaced because it is unusable. In conventional systems, replacement of the pipetting needle often entails considerable technical knowhow, which can be provided only by a specially trained maintenance technician. For example, it is not just the pipetting needle itself and other mechanical parts that have to be replaced, but also the motor and the eccentric bearing. This involves quite considerable expenditure in terms of time and/or cost. It is therefore also of particular importance from an economic point of view that the needle according to the invention can be replaced in a way that is particularly easy and uncomplicated, since this allows the operating personnel working on the analyzer to replace a damaged pipetting needle quickly and easily without calling on the assistance of a specially trained technician.

In another advantageous embodiment, the pipetting device comprises a second resetting element, wherein the second resetting element can fix the blade and the prism bearing in a stable position and releasably connect them. This has the advantage that the pipetting needle can be fixed repeatedly in a precisely defined position, and a releasable connection between the blade and the prism bearing is easy to produce and to release.

The second resetting element is preferably a spring element, particularly preferably a leaf spring. This has the advantage that the resetting element can be produced particularly easily and cost-effectively.

In an advantageous embodiment, the vibration generator comprises an eccentrically rotating shaft, which can engage in a recess of the first connection element. This has the advantage that the connection between the vibration generator and the pipetting needle is particularly easy to produce and to release. Moreover, this has the advantage that the transmission of vibrations from the vibration generator to the pipetting needle by means of the first connection element is possible in a particularly simple way.

The eccentrically rotating shaft can be an eccentric shaft, for example.

Advantageously, the eccentric bearing comprises at least one ball bearing. The contact between the eccentrically rotating shaft and the edge of the recess of the first connection element, in which the eccentrically rotating shaft at least partially engages, is preferably produced by means of the ball bearing. This ball bearing is also referred to as the eccentric ball bearing. This has the advantage that wear of the eccentric ball bearing or of the edge of the recess of the first connection element is minimized. Moreover, any frictional forces that arise are minimized.

A first sensor is preferably provided which detects the position of the eccentrically rotating shaft. This has the advantage of being able to ensure that the pipetting needle is located in the vertical position, or within a defined deviation from the vertical position, after a shaking process. Precise positioning of the pipetting needle is thereby possible. This also avoids a situation in which the eccentrically rotating shaft of the vibration generator happens to come to a standstill in a position in which the pipetting needle does not lie sufficiently perpendicularly and in which precise positioning of the pipetting needle would not be possible.

The first sensor is preferably a Hall sensor. This has the advantage that the position of the eccentrically rotating shaft can be detected particularly easily and reliably. In an advantageous embodiment, a magnet or a plurality of magnets is connected to the eccentrically rotating shaft, and their magnetic field can be detected by the Hall sensor.

In another preferred embodiment, the vibration generator comprises at least one motor. This has the advantage that the generation of vibrations can be effected in an automated manner which is particularly simple and cost-effective. The motor is preferably an electric motor. This has the advantage that the generation of vibrations can be generated, regulated and monitored electronically in a particularly easy manner.

In another preferred embodiment, the vibration generator comprises an eccentric mechanism in which a motor, preferably an electric motor, drives an eccentric bearing and an eccentric ball bearing with an eccentrically rotating shaft.

In another advantageous embodiment, the first resetting element comprises at least one spring element, preferably a helical spring. This has the advantage that the first resetting element can have a particularly simple and cost-effective configuration.

In a particularly preferred embodiment, the pipetting needle is movable with the first connection element in the direction of the longitudinal axis of the pipetting needle. This has the advantage that the pipetting needle, if incorrectly placed in a vessel, for example, or on an assembly of the analyzer, can move correspondingly, and damage to the pipetting needle and/or to the item on which the pipetting needle is incorrectly placed can be avoided or at least limited.

A second sensor, preferably a microswitch or a Hall sensor, is preferably provided which detects a movement of the pipetting needle in the direction of the longitudinal axis of the pipetting needle relative to the holder. This has the advantage that, if the pipetting needle is placed incorrectly, the second sensor can trigger a signal and, for example, the motor moving the pipetting needle in the direction of the longitudinal axis of the pipetting needle can be switched off. Thus, damage to the pipetting needle and/or to the item on which the pipetting needle is placed can be avoided or at least limited.

In another advantageous embodiment, the first securing element has at least one grip, preferably at least two grips, for replacing the pipetting needle. This has the advantage that the pipetting needle can be replaced particularly easily and comfortably by hand.

The pipetting needle is preferably heatable and/or coolable. This has the advantage, for example, that sample fluid or reagent fluid in the pipetting needle can be temperature-controlled and, for example, heated or cooled to a defined temperature.

In an advantageous embodiment, the holder, the first connection element, the first securing element, the second connection element, the pipetting needle, the suspension of the vibration generator and/or the handle or handles, for example, comprise injection-molded plastics parts. This has the advantage that assembly and parts costs can be reduced.

Another subject of the invention is an analysis appliance which comprises an aforementioned pipetting device according to the invention.

A further subject of the invention is the use of a pipetting device according to the invention in an automatic analysis appliance.

Within the meaning of the invention, a "sample" is to be understood as the material that is suspected to contain the substance to be detected (the analyte). The term "sample" comprises in particular biological liquids of humans or animals, e.g., blood, plasma, serum, sputum, exudate, bronchoalveolar lavage, lymph fluid, synovial fluid, seminal fluid, cervical mucus, feces, urine, cerebrospinal fluid, but also, for example, tissue or cell culture samples that have been suitably prepared by homogenization or cell lysis for photometric determination, preferably nephelometric determination. Moreover, plant liquids or tissues, forensic samples, water and waste water samples, foods and pharmaceuticals, for example, can also serve as samples which, if appropriate, are intended to undergo a corresponding preliminary sample treatment step before the determination.

Quantitative detection involves measuring the amount, the concentration or the activity of the analyte in the sample. The expression "quantitative detection" also covers semi-quantitative methods, which can detect only the approximate amount, concentration or activity of the analyte in the sample or can serve only to provide a relative indication of amount, concentration or activity. Qualitative detection is to be understood as the detection of the actual presence of the analyte in the sample, or the indication that the amount, concentration or activity of the analyte in the sample is below or above a defined threshold value or several defined threshold values.

BRIEF DESCRIPTION OF THE DRAWINGS

Persons skilled in the art will understand that the drawings, described below, are for illustrative purposes only. The drawings are not necessarily drawn to scale and are not intended to limit the scope of this disclosure in any way.

Identical parts are provided with the same reference signs in all of the figures.

DETAILED DESCRIPTION

Figure 1:
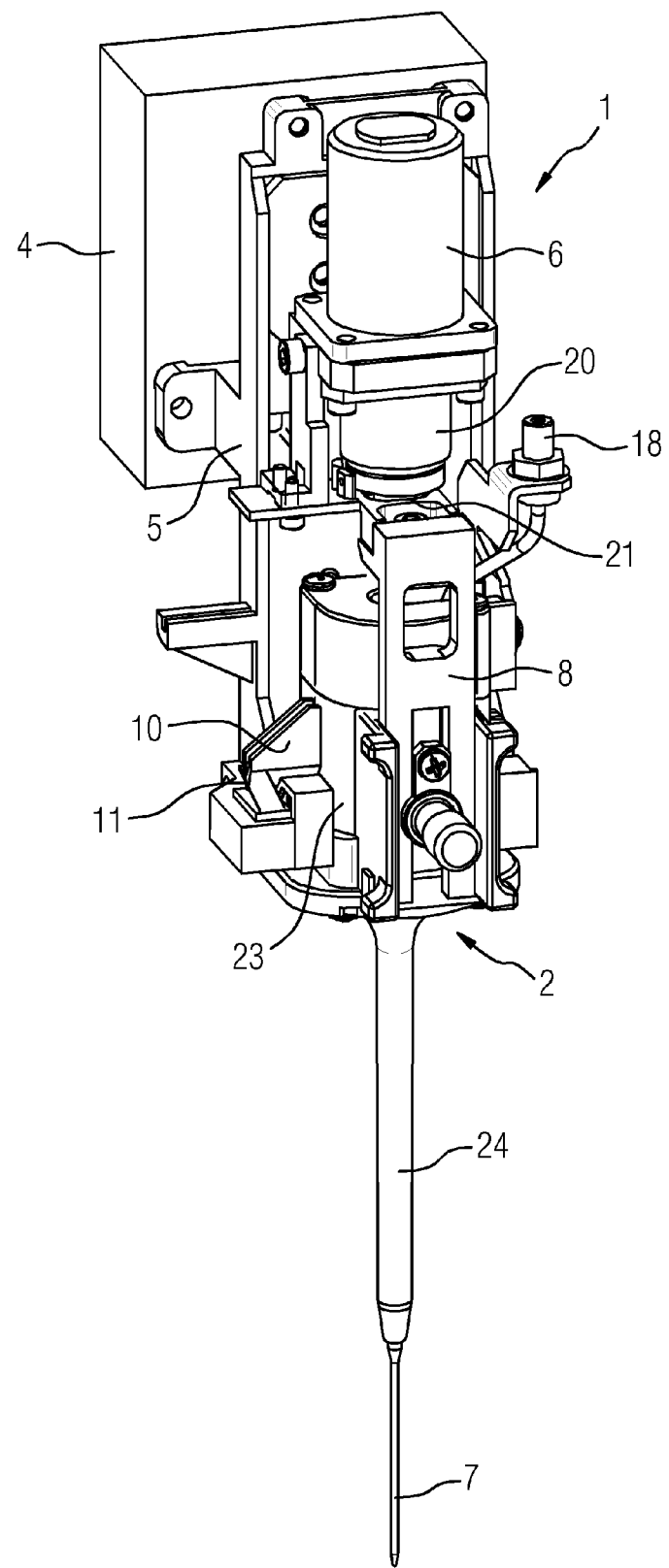
FIG. 1 shows a schematic view of the structure of the pipetting device (1) with a pipetting needle (2) inserted in the holder (5)

The pipetting device (1) according to FIG. 1 is embedded in an analysis appliance (not shown) which is designed to perform a large number of analyses of samples. For this purpose, the automatic analysis appliance comprises a large number of pipetting devices (not shown) and transport devices (not shown) and also a control unit for automated evaluation of the analyses.

The pipetting device (1) comprises the movable device (4), which is designed as an automatically movable robot arm, the holder (5) with the vibration generator comprising the eccentric bearing (20), the motor (6), and also the pipetting needle (2). The pipetting needle (2) comprises a pipette inlet (18), a suspension (23) and a needle body (24) with a tip (7). The pipetting needle (2) is releasably connected to the holder (5) by means of the first securing element (10). The holder (5) is secured on the movable device (4). The first securing element (10) is designed as a blade and rests on a second securing element (11), which is designed as a prism bearing. The first connection element (8) comprises a recess (21).

Figure 2:
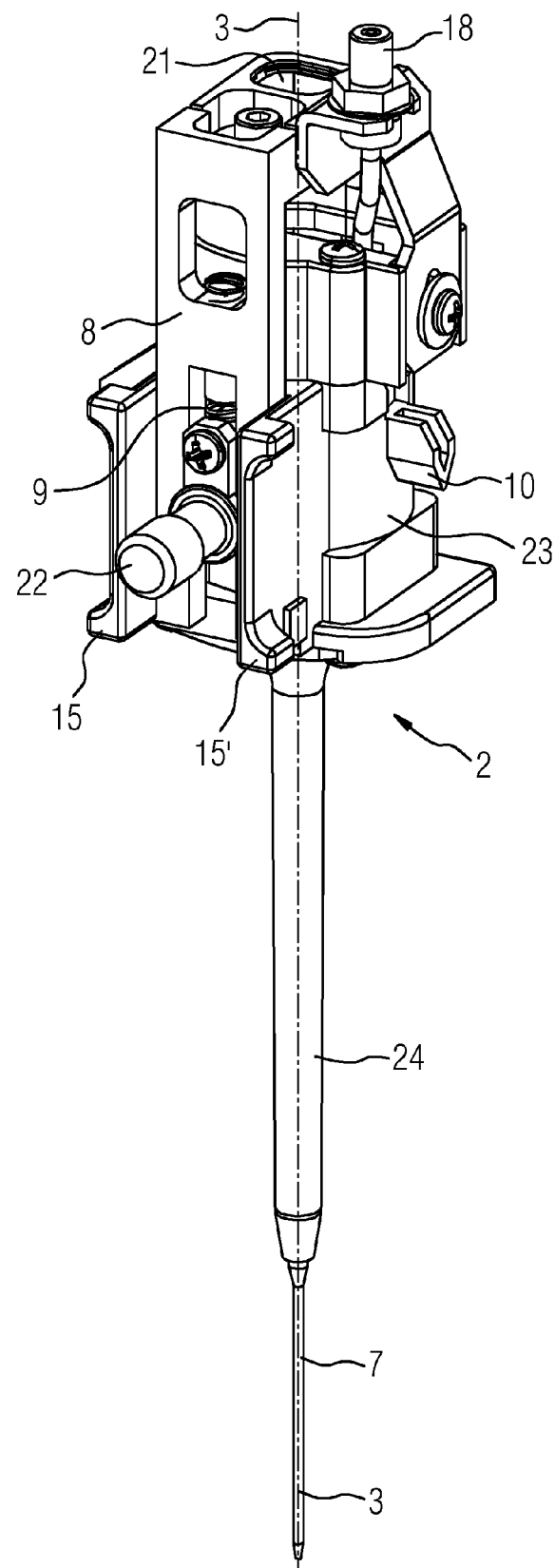
FIG. 2 shows a schematic view of the structure of the pipetting needle (2) and the first connection element (8)

FIG. 2 shows the pipetting needle (2) with the tip (7), the needle body (24), the suspension (23) and the pipette inlet (18), and also the first securing element (10), which is designed as a blade, and the first connection element (8). The first connection element (8) comprises the recess (21) and the first resetting element (9). The first securing element (10) is mounted laterally on the suspension (23), in the upper part of the latter. The direction of the longitudinal axis (3) of the pipetting needle (2) is indicated as a dot-and-dash line. Moreover, a clamping screw (22) is shown.

Figure 3:
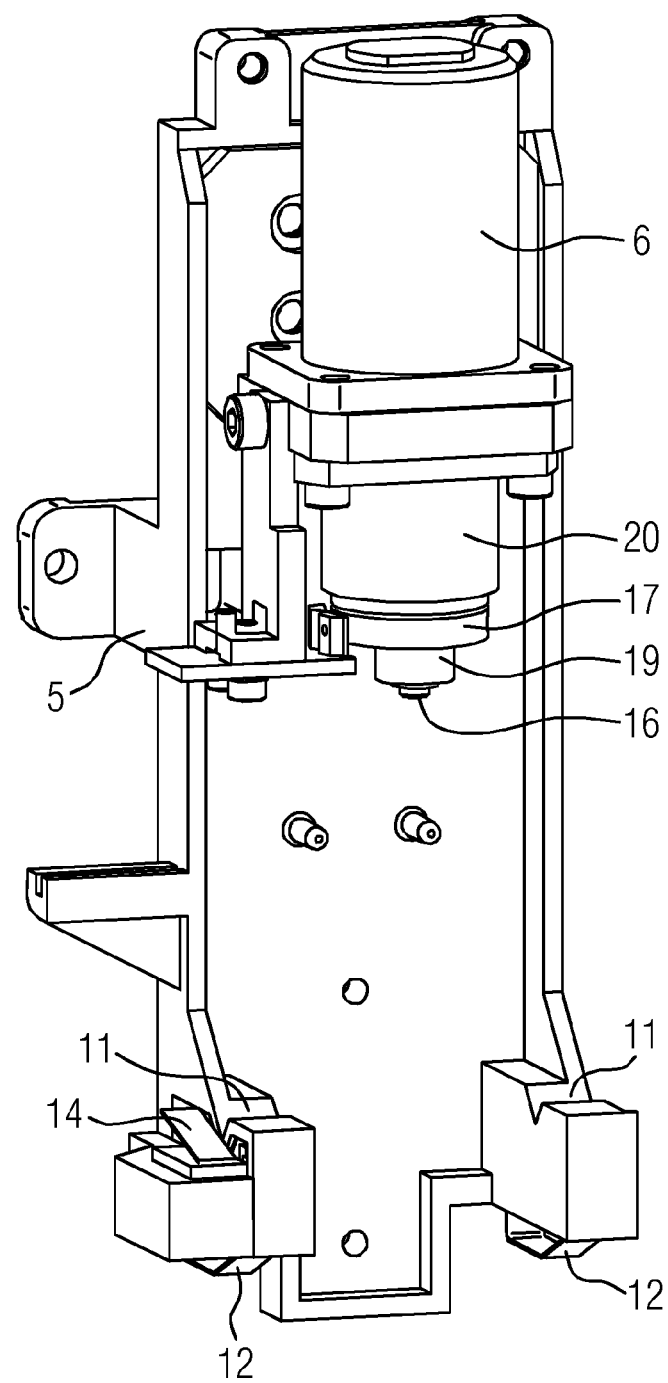
FIG. 3 shows a schematic view of the structure of the holder (5) with vibration generator, without an inserted pipetting needle (2)

FIG. 3 shows the holder (5), which is mounted on the movable device (4) (not shown). The vibration generator comprises a motor (6), which drives the eccentric bearing (20) and the eccentric ball bearing (19) with the eccentrically rotating shaft (16), wherein the motor (6) is secured on the holder (5). The holder (5) comprises two prism bearings (11), each with a second resetting element (12) (only partly visible) designed as a spring element, and the first sensor (14), which is designed as a microswitch. Moreover, a magnet (17) is mounted laterally in the lower area of the eccentric bearing (20) in the direction of the eccentric ball bearing (19).

Figure 4:
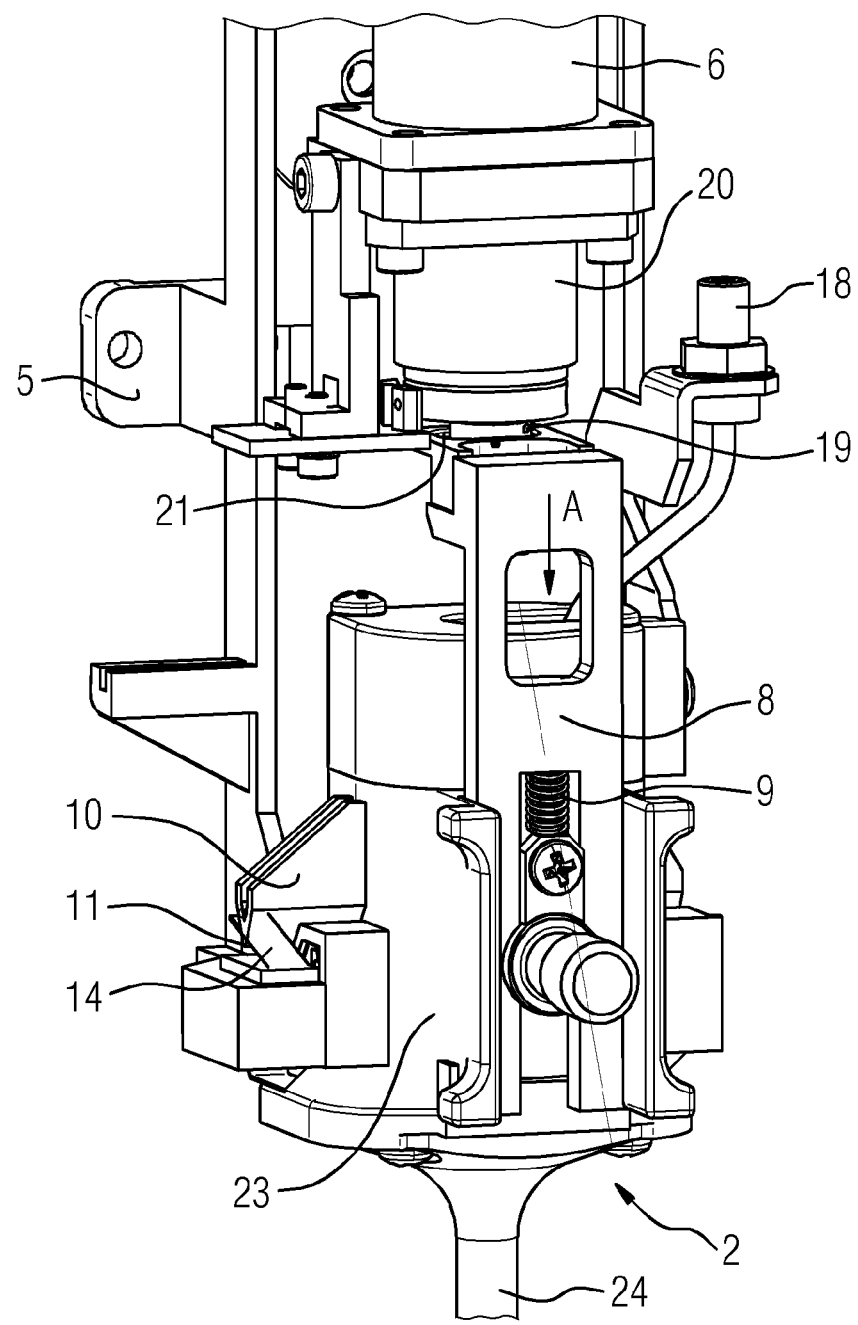
FIGS. 4, 7 and 8 show schematic views of details of the pipetting device (1) with a pipetting needle (2) inserted in the holder (5)

FIG. 4 shows a detail of the pipetting device (1) with, inserted in the holder (5), a pipetting needle (2) with the pipette inlet (18), the suspension (23), and a part of the needle body (24). The first securing element (10) is designed as a blade, and the second securing element (11) is designed as a prism bearing. The first connection element (8), which is designed as an angle piece, comprises the recess (21) and is located in the rest position and is not deflected downward from the rest position in direction A of the arrow toward the first resetting element (9). The releasable connection between the eccentric ball bearing (19) with the eccentrically rotating shaft (16) (not shown) of the shaking device and the first connection element (8) is produced, and there is direct contact between the eccentric ball bearing (19) and the edge of the recess (21) in the first connection element (8). Moreover, the eccentric bearing (20) is shown. In the area of the prism bearing (11), a second sensor (14), which is designed as a microswitch, is mounted on the holder (5). The microswitch triggers if the pipetting needle (2) sits incorrectly and the blades (10), which are secured laterally on the suspension (23), are pressed out along the longitudinal axis (3) from the prism bearing (11).

Figure 5:
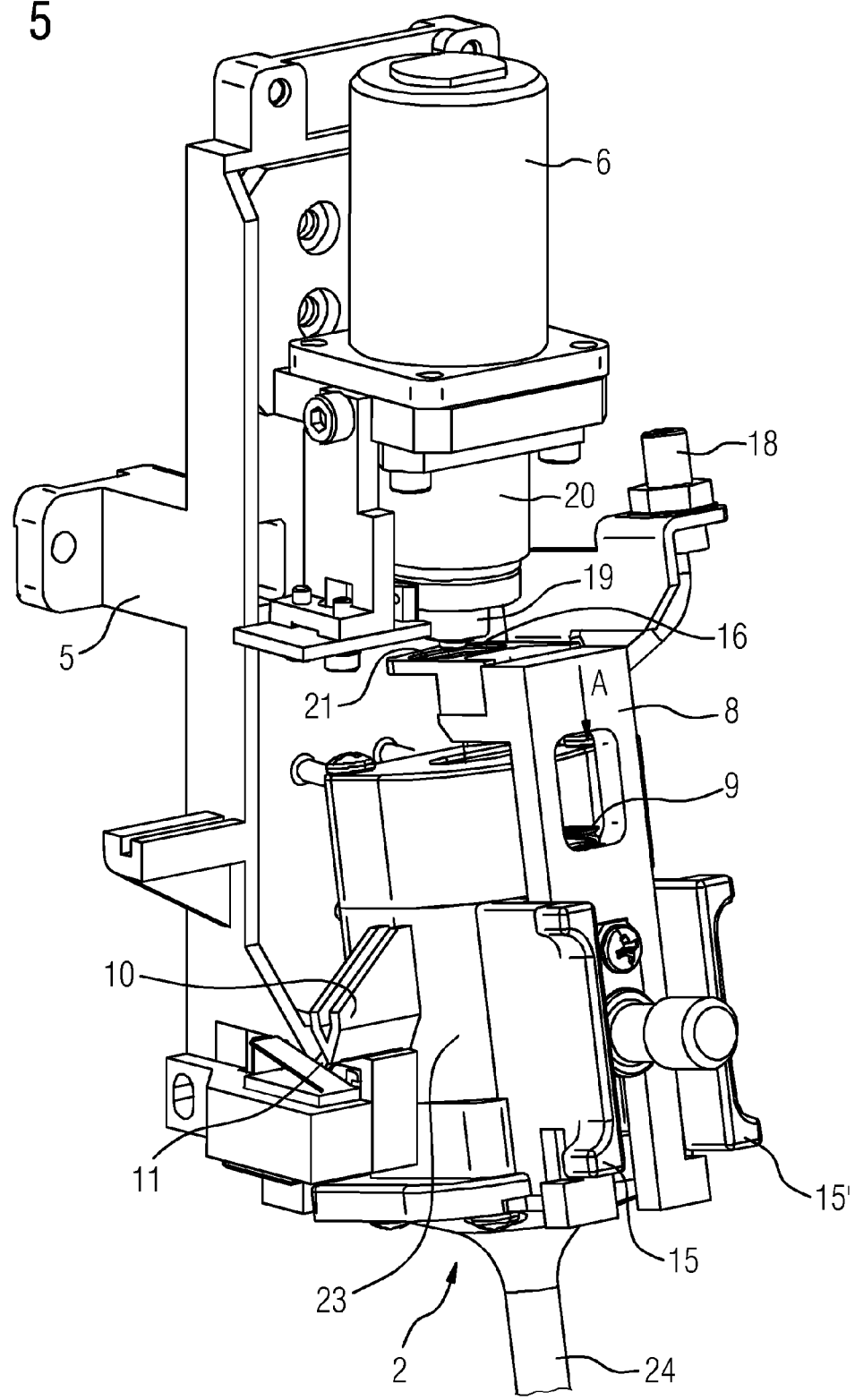
FIGS. 5 and 6 show schematic views of details of the pipetting device (1) during the insertion or removal of the pipetting needle by producing or releasing the connection between the holder (5) and the pipetting needle (2).

FIG. 5 shows a detail of the pipetting needle (2) with pipette inlet (18), suspension (23), a part of the needle body (24) and also the holder (5), during the insertion of the pipetting needle (2) into the holder (5). The pipetting needle (2) is set obliquely and the blade of the first securing element (10) is located in spatial proximity to the prism bearing of the second securing element (11), although the blade is not yet located in the prism bearing. The grips (15, 15') in this case facilitate the manual insertion (or also the removal) of the pipetting needle (2) from the holder (5). The first connection element (8), which is designed as an angle piece, is deflected downward from the rest position, in the direction A of the arrow, toward the first resetting element (9). The releasable connection between the eccentric ball bearing (19) with the eccentrically rotating shaft (16) of the shaker device and of the first connection element (8) is released, and there is no direct contact between the shaft (16) and the first connection element (8). Moreover, the eccentric bearing (20) is shown. The eccentric ball bearing (19) and the edge of the recess (21) in the first connection element (8) can be brought into releasable contact with each other.

Figure 6:
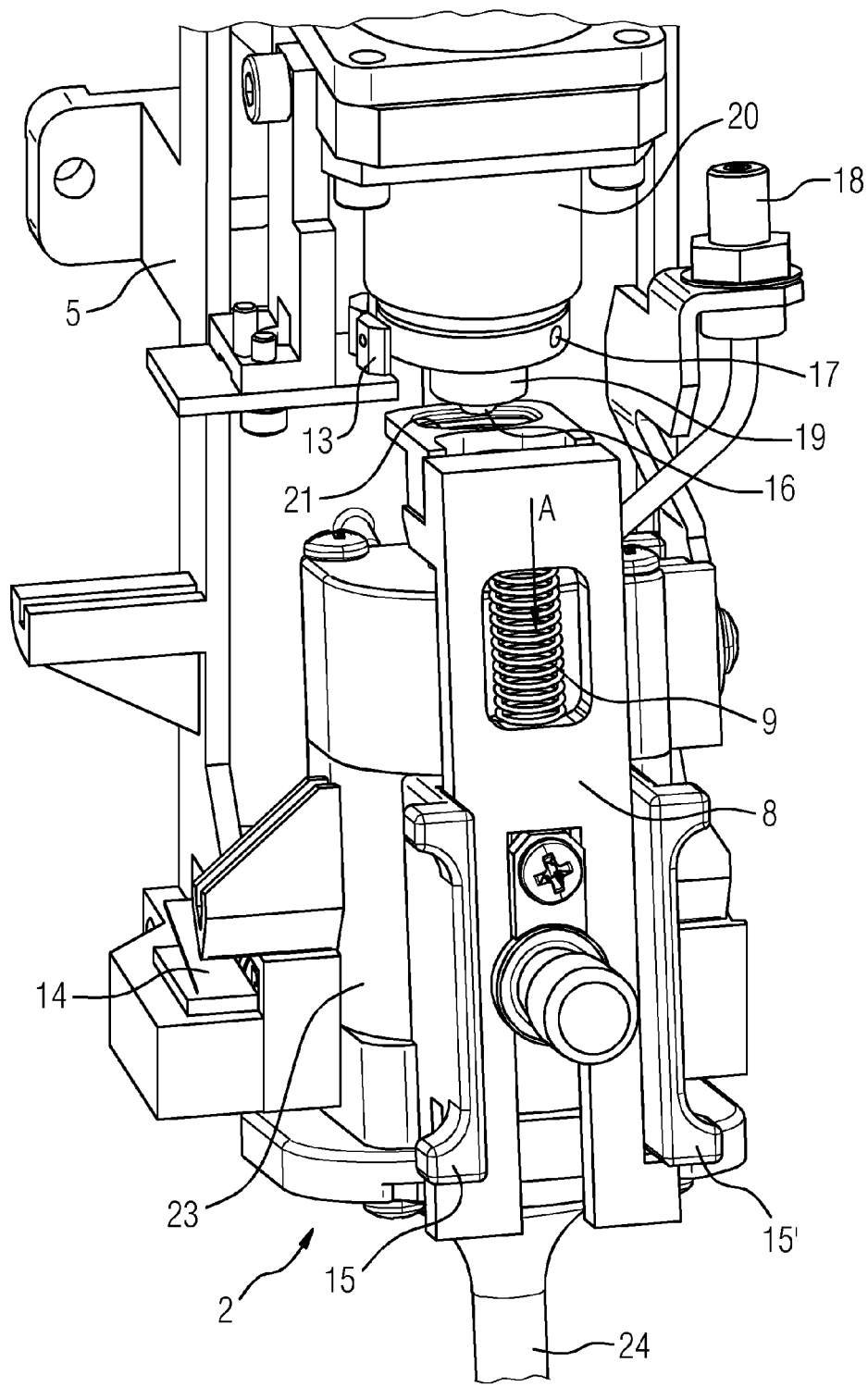

The parts shown in FIG. 5 are shown from a different angle in FIG. 6, except that the motor (6) of the shaker device is not shown. Moreover, FIG. 6 shows the first sensor (13), which is mounted on the holder (5) in spatial proximity to the eccentric drive (20) and eccentric ball bearing (19). The magnet (17) is mounted laterally in the direction of the eccentric ball bearing (19) in the lower area of the eccentric bearing (20), such that the magnet (17) interacts with the sensor (13), depending on the position of the eccentrically rotating shaft (16), and therefore the position of the eccentrically rotating shaft (16) or the position of the eccentric ball bearing (19) can be determined.

Figure 7:
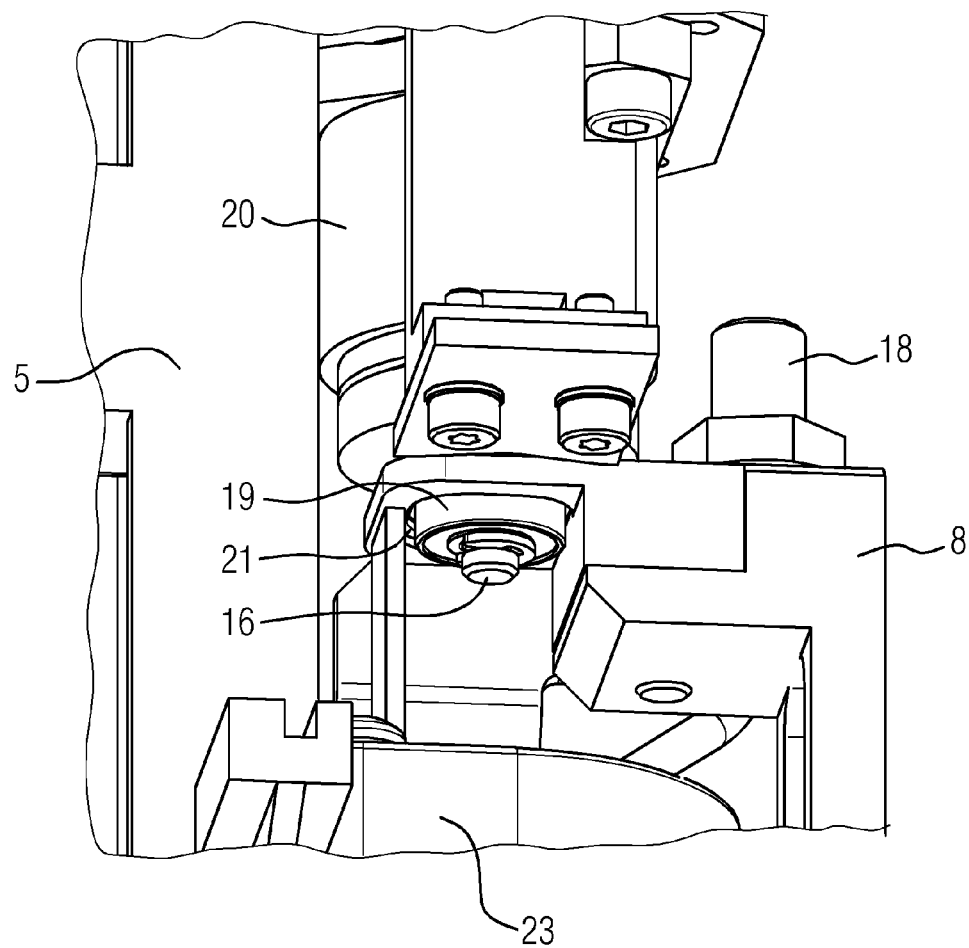

FIG. 7 shows a detail of the pipetting device (1) seen obliquely from below, with a pipetting needle (2) inserted into the holder (5), wherein the pipette inlet (18) of the pipetting needle (2) and the suspension (23) are partly visible. The first connection element (8), which is designed as an angle piece, comprises the recess (21) and is located in the rest position. The releasable connection between the eccentric ball bearing (19) with the eccentrically rotating shaft (16) of the vibration generator and the first connection element (8) is produced, and there is direct contact between the eccentric ball bearing (19) and the edge of the recess (21) in the first connection element (8). The eccentric bearing (20) is also shown.

Figure 8:
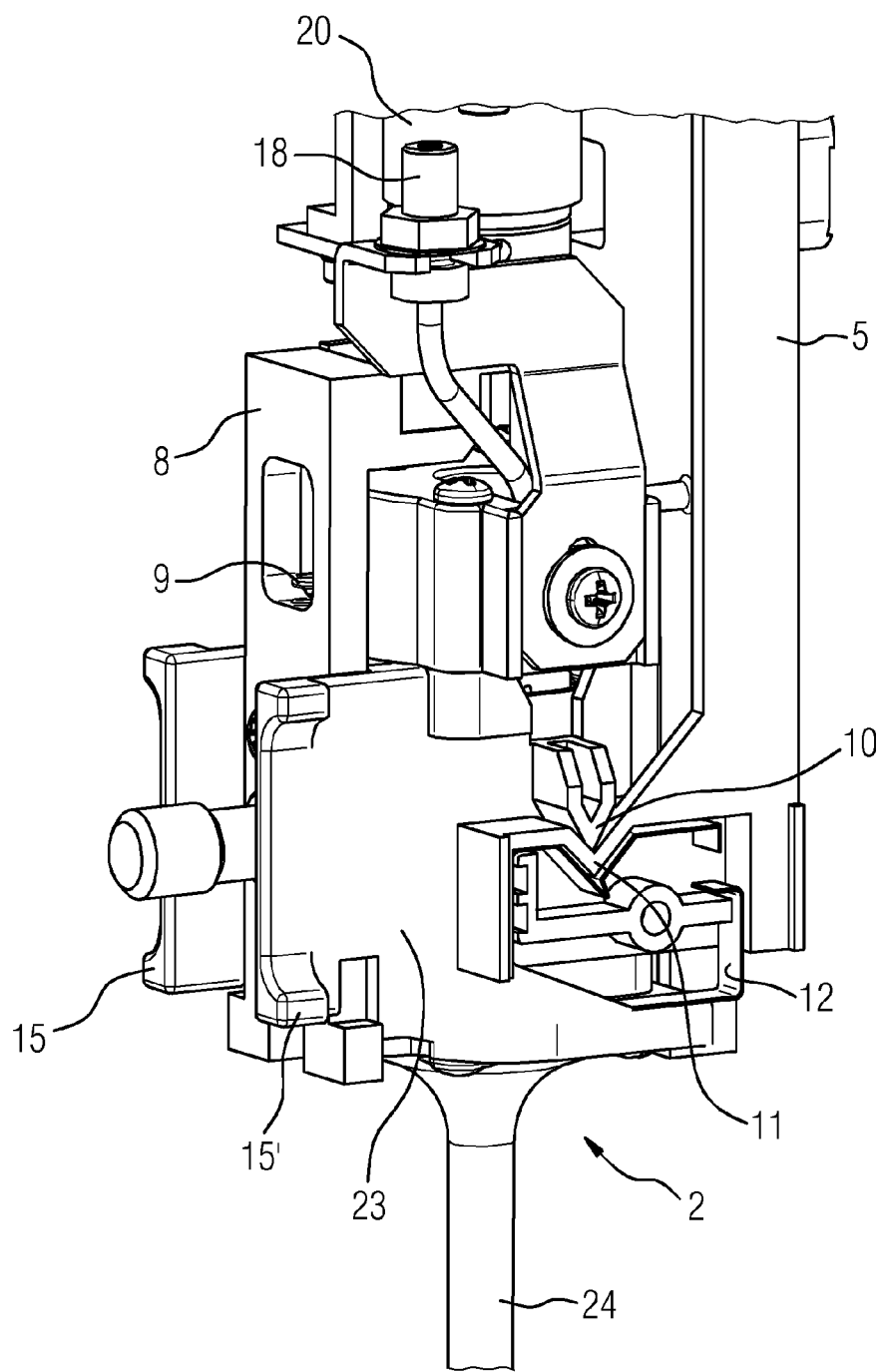

FIG. 8 shows a detail of the pipetting needle (2) and of the holder (5), with the pipetting needle (2) inserted in the holder (5), with two grips (15, 15') and with the first connection element (8). The blade of the first securing element (10) is located in the prism bearing of the second securing element (11). The second resetting element (12), which is designed as a spring element, exerts a restoring force and holds the blade in the prism bearing.

LIST OF REFERENCE SIGNS 1 pipetting device
2 pipetting needle
3 longitudinal axis
4 movable device
5 holder
6 motor
7 tip
8 first connection element
9 first resetting element
10 first securing element
11 second securing element
12 second resetting element
13 first sensor
14 second sensor
15,15' grip
16 shaft
17 magnet
18 pipette inlet
19 eccentric ball bearing
20 eccentric bearing
21 recess
22 clamping screw
23 suspension
24 needle body
A direction

What is claimed is:

1. A pipetting device for an automatic analysis appliance, the pipetting device comprising:
    a pipetting needle with a longitudinal axis for the pipetting of liquids, the pipetting needle having a tip,
    a movable device that is movable in the direction of the longitudinal axis of the pipetting needle and in at least one direction perpendicular to the direction of the longitudinal axis of the pipetting needle and that is used for moving the pipetting needle within at least one range of movement,
    a holder for the pipetting needle, wherein the holder is mounted on the movable device and to which the pipetting needle is releasably connected, and
    a vibration generator that can set at least the tip of the pipetting needle in vibration,
    wherein the vibration generator is mounted on the movable device or on the holder and is configured to set at least the tip of the pipetting needle in vibration during a transfer of the pipetting needle by the movable device from a first position to a second position in the at least one direction perpendicular to the direction of the longitudinal axis.

2. The pipetting device as claimed in claim 1, wherein the pipetting device comprises a movable first connection element with a first resetting element, and the first connection element produces a releasable connection between the pipetting needle and the vibration generator.

3. The pipetting device as claimed in claim 2, wherein the first connection element has a shape of an angle piece.

4. The pipetting device as claimed in claim 1, wherein the pipetting device has a first and a second securing element, the pipetting needle comprises a suspension, the first securing element is mounted laterally on the suspension and comprises a blade, and the second securing element is mounted on the holder and comprises a prism bearing.

5. The pipetting device as claimed in claim 4, wherein the pipetting device comprises a second resetting element, and wherein the second resetting element fixes the blade and the prism bearing in a stable position and releasably connects them.

6. The pipetting device as claimed in claim 2, wherein the vibration generator comprises an eccentrically rotating shaft that can engage in the first connection element.

7. The pipetting device as claimed in claim 6, further comprising a first sensor that detects the position of the eccentrically rotating shaft.

8. The pipetting device as claimed in claim 1, wherein the vibration generator comprises at least one motor.

9. The pipetting device as claimed in claim 2, wherein the first resetting element comprises at least one spring element.

10. The pipetting device as claimed in claim 2, wherein the pipetting needle is movable with the first connection element in the direction of the longitudinal axis of the pipetting needle.

11. The pipetting device as claimed in claim 1, further comprising a second sensor that detects a movement of the pipetting needle in the direction of the longitudinal axis of the pipetting needle.

12. The pipetting device as claimed in claim 4, wherein the first securing element has at least one grip for replacing the pipetting needle.

13. The pipetting device as claimed in claim 1, wherein the pipetting needle is heatable.

14. An automatic analysis appliance comprising a pipetting device as claimed in claim 1 and a control unit for automated evaluation of analyses performed by the automatic analysis appliance.

15. A method of using a pipetting device as claimed in claim 1 in an automatic analysis appliance, the method comprising:
   transferring the pipetting needle with the movable device from the first position to the second position; and
   vibrating at least the tip of the pipetting needle during the transferring.

16. The pipetting device as claimed in claim 5 wherein the second resetting element comprises a spring element or a leaf spring.

17. The pipetting device as claimed in claim 7 wherein the first sensor comprises a Hall sensor.

18. The pipetting device as claimed in claim 8, wherein the at least one motor comprises an electric motor.

19. The pipetting device as claimed in claim 9, wherein the at least one spring element comprises a helical spring.

20. The pipetting device as claimed in claim 11, wherein the second sensor comprises a microswitch or a Hall sensor.

* * * * *